United States Patent [19]
Alvord et al.

[11] Patent Number: 5,558,846
[45] Date of Patent: Sep. 24, 1996

[54] APPARATUS FOR DISINFECTING CONTACT LENSES HAVING IMPROVED VENT MEANS

[75] Inventors: Larry A. Alvord, Lawrenceville, Ga.; Robert F. McCoy, Maplewood, N.J.

[73] Assignee: Ciba Geigy Corporation, Tarrytown, N.Y.

[21] Appl. No.: 349,719

[22] Filed: Dec. 5, 1994

[51] Int. Cl.⁶ .............................. A61L 2/16; B65D 51/16
[52] U.S. Cl. .................... 422/301; 422/113; 422/297; 206/5.1; 220/203.09; 220/203.11; 134/901
[58] Field of Search ............... 206/5.1; 134/901; 220/203.09, 203.16, 203.11; 422/113, 117, 297, 300, 301, 296; 435/304.1, 305.3, 305.4

[56] References Cited

U.S. PATENT DOCUMENTS

| | | | |
|---|---|---|---|
| 3,912,451 | 10/1975 | Gaglia, Jr. | |
| 4,396,583 | 8/1983 | LeBoeuf | 206/5.1 X |
| 4,483,439 | 11/1984 | Steigerwald et al. | 220/203.11 X |
| 4,637,919 | 1/1987 | Ryder et al. | 422/300 |
| 4,750,610 | 6/1988 | Ryder | 206/5.1 |
| 4,889,693 | 12/1989 | Su et al. | 206/438 X |
| 4,956,156 | 9/1990 | Kanner et al. | 422/300 |
| 4,981,657 | 1/1991 | Ryder | 422/310 |
| 4,996,156 | 2/1991 | Kanner | 422/113 |
| 5,164,166 | 11/1992 | Stepanski et al. | 422/301 X |
| 5,186,317 | 2/1993 | Ryder et al. | 422/301 X |
| 5,250,266 | 10/1993 | Kanner | 422/113 |

Primary Examiner—Robert J. Warden
Assistant Examiner—E. Leigh Dawson
Attorney, Agent, or Firm—Edward McC. Roberts; R. Scott Meece; Michael U. Lee

[57] ABSTRACT

An ophthalmic lens disinfection apparatus, including a container and a mating cap, she apparatus having an improved seal and vent means for venting gas generated within the apparatus. The vent means is an integral part of the disinfection apparatus which allows venting of gas when internal pressure increases, while maintaining a seal which is substantially gas and liquid-impermeable at other times. The seal is defined by the interference mating of a flexible periphery on a container with a rigid mating rim on a cap. The apparatus is particularly useful in the disinfection of contact lenses with hydrogen peroxide in which the excess peroxide is decomposed into water and oxygen.

26 Claims, 2 Drawing Sheets

APPARATUS FOR DISINFECTING CONTACT LENSES HAVING IMPROVED VENT MEANS

BACKGROUND OF THE INVENTION

1. Field of the Invention

This invention relates broadly to ophthalmic lens treatment technology. More specifically, this invention relates to contact lens disinfecting devices in which gas is liberated during the disinfection process.

2. Description of the Related Art

Contact lenses provide the consumer with an exceptionally convenient alternative to spectacles or glasses, a more archaic form of vision correction. However, proper maintenance of contact lenses require periodic sterilizing or disinfecting to eliminate harmful bacteria or fungi, and cleansing to remove deposits such as proteins or lipids which adhere to the lens. In order to clean and/or disinfect contact lenses, a wide variety of devices have been developed.

A particularly efficacious method of disinfecting contact lenses is by a chemical treatment of the lenses with a hydrogen peroxide solution, as described in U.S. Pat. No. 3,912,451, issued to Gaglia, Jr., Oct. 14, 1975. In a typical lens disinfecting apparatus, contact lenses are placed in hydrogen peroxide solution inside a container. The container is sealed (e.g., by threads on the container mating with threads on a cap) for a predetermined period of time to sufficiently disinfect the lenses, with the seat preventing liquid spillage resulting from container movement.

Although hydrogen peroxide is highly effective in disinfecting contact lenses, hydrogen peroxide must be removed from lenses prior to placing the lenses in a patient's eye in order to avoid patient discomfort. One method of removing hydrogen peroxide involves contacting the hydrogen peroxide with a platinum catalyst, thereby rapidly decomposing the hydrogen peroxide into water and gaseous oxygen. Liberated gaseous oxygen resulting from the peroxide decomposition generates internal pressure in the cleaning container which must be vented. In order to alleviate this pressure, a wide variety of venting means have been developed.

For example, U.S. Pat. No. 4,637,919, issued to Ryder, et al., Jan. 20, 1987, discloses a contact lens cleaning container and mating cap, where the cap includes a filter assembly positioned in a vent passageway. The filter assembly includes a hydrophobic membrane which continuously vents the gas generated within the container during the decomposition of peroxide. The pores in the hydrophobic membrane are sufficiently small to inhibit liquid leakage from the container.

U.S. Pat. No. 4,750,610, issued to Ryder, Jun. 14, 1988, discloses a disinfecting container which is affixed to a cap via loose threading. The cap includes a resiliently deflectable flange which acts as a check valve in conjunction with the container. In operation, the cap flange is typically in a closed position, i.e., the flange is positioned immediately adjacent a portion of the container, thereby preventing liquid leakage. When excess internal pressure develops, the cap flange deflects, allowing gas to pass through the loosely threaded container-cap connection to the outside of the container.

U.S. Pat. No. 4,956,156, issued to Kanner, et al., Sep. 11, 1990, discloses a disinfecting system which includes a cap having a bore. A post is positioned in the bore with a resiliently-deflectable diaphragm positioned around the post. The diaphragm-post seal prevents liquid leakage, while allowing gas to pass upon deflection of the diaphragm when sufficient internal pressure develops.

U.S. Pat. No. 4,996,027, issued to Kanner, Feb. 26, 1991, discloses a disinfecting system which includes a container and cap connected by threading. A self-reseating unitary gasket is positioned between the cap and container to provide a liquid-tight seal. Increased internal pressure causes the gasket to unseat, at least partially, allowing gas to pass between the cap and container connection to the environment.

U.S. Pat. No. 5,250,266, issued to Kanner, Oct. 5, 1993, discloses a lens cleaning apparatus, including a container and a cap, in which gas is vented through a type of check valve in the cap. The check valve includes a disc having a linear slit therethrough. The slit generally provides a liquid-impermeable barrier, but when internal pressure is generated, the slit opens to allow gas to pass to the environment.

The previously-described patents describe practical venting alternatives for peroxide-based lens cleaning/disinfecting devices. However, there is a need to provide a less complicated venting system, both from a manufacturing perspective and from an operational perspective.

SUMMARY OF THE INVENTION

An object of the invention is to provide a sealing and venting means for a chemical disinfection apparatus in which gas is liberated during the disinfection process, where the vent means provides a seal which is substantially liquid-impermeable in the absence of applied internal pressure.

Another object of the invention is to provide a disinfection apparatus sealing and venting means which can be manufactured in the absence of complicated equipment or process steps.

A further object of the invention is to provide a lens disinfecting apparatus sealing and venting means which is an integral part of the disinfection apparatus.

Yet another object of this invention is to provide a lens disinfecting apparatus vent means having an insubstantial probability of failure.

Another object of this invention is to provide a simplified lens cleaning apparatus sealing and venting means which does not require additional components specific to the sealing and venting means.

The invention is an ophthalmic lens disinfection apparatus having an improved sealing and venting means for use with disinfecting solutions which liberate gas during or after the disinfection process. The apparatus includes a container having an open end adapted to receive a disinfecting solution and a contact lens retaining means holding one or more contact lenses. The apparatus further includes a cap adapted to mate with the container to provide a seal which is substantially liquid-impermeable. The cap includes a sealing rim adapted to mate with the periphery of the container at the open end of the container, thereby forming a primary sealing and venting means, and a secondary venting means, preferably defined by at least one opening through the cap which is positioned between the external periphery of the cap and the sealing rim. The container periphery is sufficiently flexible to permit gas to pass between the container periphery and the cap sealing rim, and ultimately, out through the hole in the cap. However, the container periphery is sufficiently rigid to provide a seal with the cap sealing rim which is substantially gas and liquid-impermeable, in the absence of excess internal pressure.

In a preferred embodiment, a cylindrical container is provided with external threads along a circular peripheral edge which defines the opening to the container. A mating cap is provided with-internal threads adapted to screw onto the container threads.

DESCRIPTION OF THE PREFERRED EMBODIMENTS

At the outset, in order to further clarify the description of the present invention, the following terms are defined for use herein. The invention is described throughout with reference to a "disinfecting" system. However, the description is for convenience and references the preferred embodiment; thus, the invention is not so limited. "Disinfecting", as used herein, refers broadly to deactivating, disabling, killing, or otherwise sterilizing microorganisms. "Cleaning", as used herein, refers to removing of deposits such as protein or lipids from a lens surface; or to some combination thereof. "Opening", as used herein, means a passageway of any shape, including without limitation, holes (i.e., openings having circular or oval shape); openings having triangular, rectangular, or other shape; gratings; or openings more properly described as slits, in which two surfaces loosely mate. "Container", as used herein, refers to any receptacle that defines an internal cavity capable of holding a quantity of liquid when positioned appropriately. "Cap", as used herein, refers to any covering adapted to mate with, and seal, a container. These definitions are incorporated to aid the reader in understanding the description of the invention; however, the terms are intended to have the broadest reasonable meaning unless otherwise expressly limited.

Figure 1:
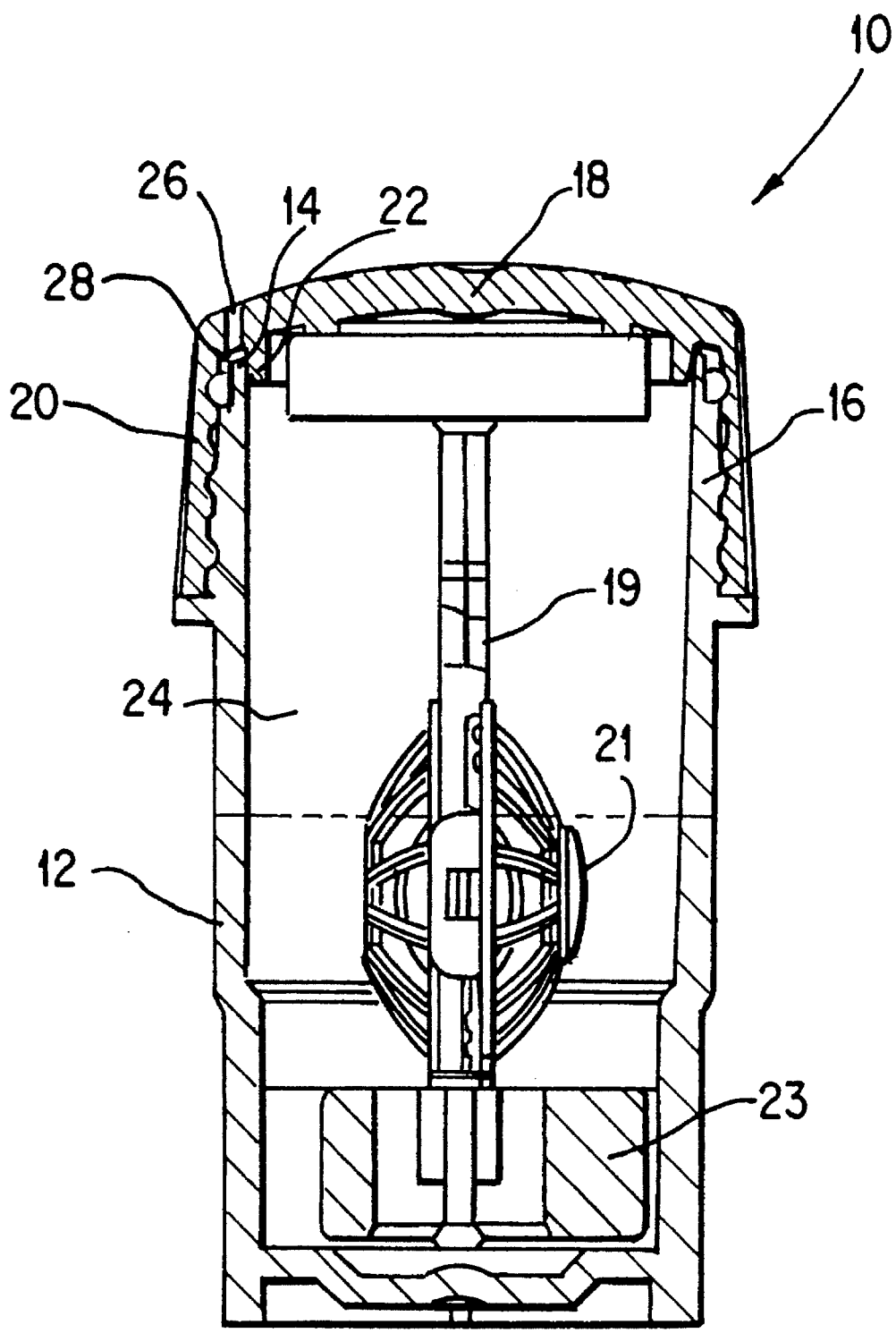
FIG. 1 is a side sectional view of one embodiment of a contact lens cleaning apparatus in accordance with the present invention.

Referring to FIG. 1, a preferred embodiment of the present lens disinfecting device 10 is shown in a side sectional view. The device includes a container 12 having an opening at one end defined by periphery 14 of the container. The container has external threading 16 near the opening defined by periphery 14. Cap 18 contains internal threading 20 adapted to mate with container threading 16 to form a seal which is substantially liquid-impermeable. While threading is a preferred means of releasably affixing the container to the cap, the present invention is not limited to such affixation means.

Cap 18 also includes a substantially circular sealing rim 22 which is positioned immediately inside and in intimate contact with container periphery 14 when device 10 is in a sealed configuration, thereby defining a lens disinfecting chamber 24. Contact of cap sealing rim 22 with container periphery 14 provides a normally-closed seal for chamber 24 which is substantially liquid-impermeable.

Cap 18 further includes an opening 26, extending from one surface of cap 18 to the other, thereby defining an unobstructed pathway from a point 28 immediately outside the container-cap seal (defined by the mating of rim 22 with periphery 14) to a point outside device 10, i.e., to the environment.

In addition, in this embodiment, cap 18 includes a lens support stem 19 holding a lens retaining means 21 and a catalytic element 23. There are numerous variations of these additional elements, some of which are more fully described in U.S. Pat. Nos. 4,637,919, 4,750,610, 4,956,156, 4,996,027, and 5,250,266, which are hereby incorporated by reference. The present invention is not limited to the structure or components required for lens retention or chemical decomposition (e.g., platinum catalytic element for peroxide decomposition).

Figure 2:
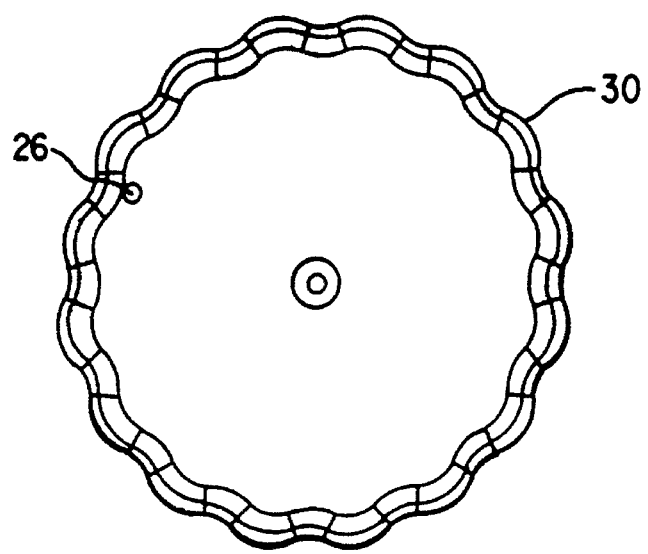
FIG. 2 is a top view of the cap of the apparatus of FIG. 1.

FIG. 2 is a top view of cap 18 illustrating the relative positions of the cap opening 26 and external periphery 30 of the cap. Opening 26 is positioned between cap sealing rim 22 (not shown) and external periphery 30.

Figure 3:
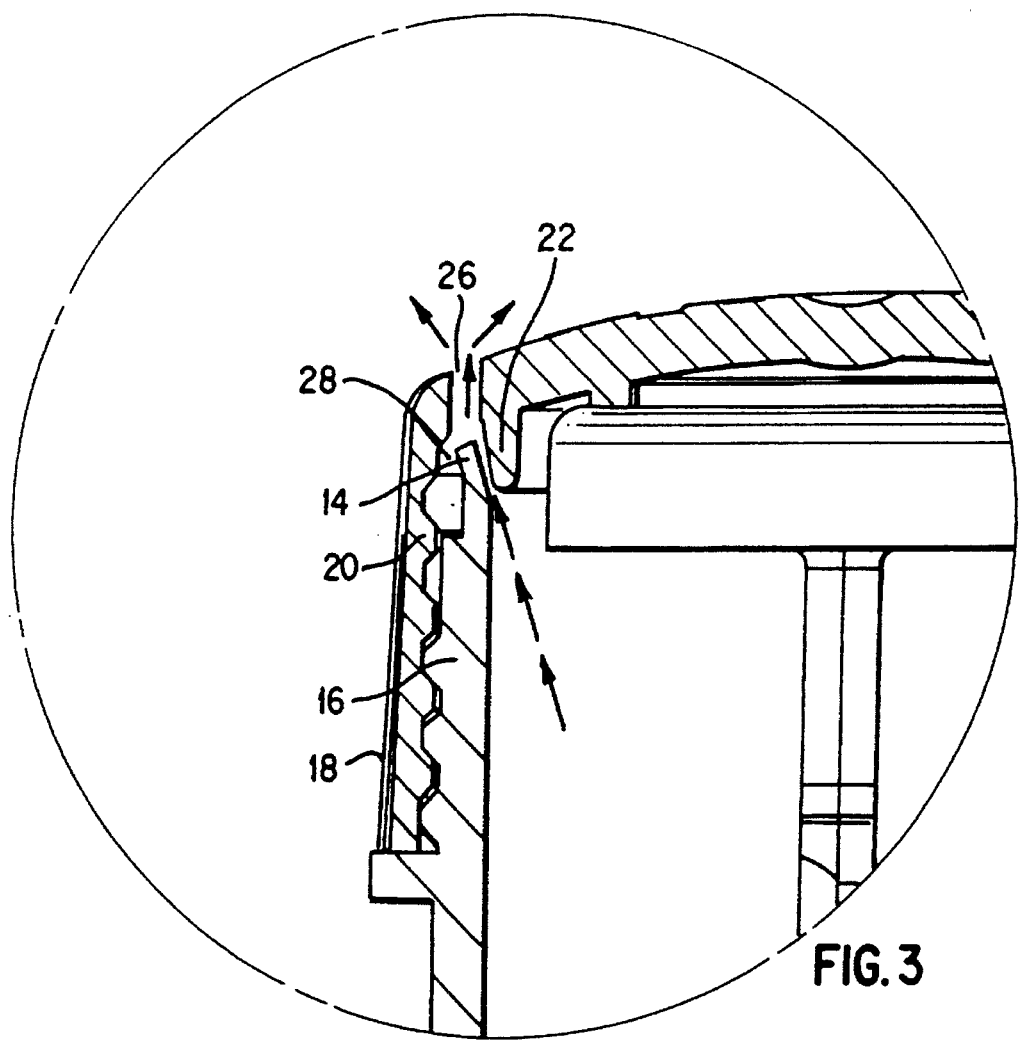
FIG. 3 is a sectional view of the vent passageway of the apparatus of FIG. 1.

FIG. 3 is a side sectional view of a portion of device 10 illustrating the vent passageway (See set of arrows) formed when container periphery 14 deflects under excess internal pressure generated within the disinfecting chamber. Gas within the chamber passes between cad sealing rim 22 and container periphery 14, through a point 28 outside chamber 24 and through cap opening 26 to the environment surrounding device 10. After the internal pressure with device 10 diminishes to a predetermined level, container periphery 14 returns to its original position in intimate contact with cap sealing rim 22.

Clearly, container periphery 14 must be sufficiently flexible to allow deformation at a predetermined difference between internal pressure and external ambient pressure. However, container periphery 14 must also be sufficiently rigid to form a normally substantially liquid-impermeable seal with cap sealing rim 22. Further, container periphery 14 must be sufficiently resilient to bend back and forth numerous times, while retaining the ability to return to a position in which container periphery 14 intimately contacts cap sealing rim 22, in order to form a liquid-impermeable, normally-closed seal.

The aforementioned properties of container periphery 14 must be considered in the selection of materials and dimensions of container 12 and periphery 14. Preferably, container 12 and container periphery 14 are formed from the same material. The container may be formed from a wide range of plastic or polymeric materials, preferably substantially transparent, including without limitation, hydrophobic polymeric materials such as polyethylene and polypropylene, especially polypropylene. While the dimensions of the container body are not crucial to the invention, the container body preferably has a cylindrical shape and a thickness ranging from about 1 mm to about 4 mm, more preferably about 1 to 2 mm. The "thickness" of the container periphery is measured along a cross-section substantially parallel with the plane defined by the container opening. Container periphery 14 may gradually reduce in thickness towards the container opening (e.g., a linear thickness reduction, producing a triangular thickness profile), or may be immediately narrowed to a predetermined constant thickness. Preferably, periphery 14 has a uniform thickness of about 0.3 to 1.5 mm, more preferably about 0.6 to about 0.9 mm. This reduced peripheral thickness preferably extends about 1 to about 10 mm, more preferably about 2 to 4 mm, along the container body from the opening of the container (See FIG. 1).

The cap and cap sealing rim may be formed from the same material as the container. Cap sealing rim 22 should be substantially rigid, thereby not deforming under excess internal device pressure, but allowing container periphery 14 to deform. Thus, the dimensions, especially the thickness, of cap sealing rim 22 are dependent on the dimensions of container periphery 14. While cap sealing rim 22 may have a wide variety of shapes and dimensions, it is preferably substantially rectangular or trapezoidal in shape, with rounded edges. While there is no upper limit on the thickness of the cap sealing rim, the thickness is preferably from about 0.75 to about 2.5 mm, more preferably about 1.0 to 2.0 mm.

Alternatively, the cap sealing rim may defined by a substantially solid disc affixed to the cap or molded to the cap during the cap formation process. The disc is affixed centrally to the side of the cap which faces the container when the cap and container are mated. The use of a solid disc further ensures that the container periphery is the component that deforms upon increased gas pressure.

The container-cap seal is defined by an interference fit between container periphery 14 and cap sealing rim 22. An interference fit is preferably achieved by sizing the internal diameter of container periphery 14 slightly less than the external diameter of sealing rim 22. Thus, the external diameter of the cap sealing rim is sized sufficiently larger than the internal diameter of the container periphery such that the container periphery deforms slightly when mated with the cap sealing rim, thereby providing a seal to the container which is substantially impermeable to liquid and gas in the absence of excessive internal pressure. When the cap is affixed to the container, the flexible plastic of container periphery 14 deforms slightly, thereby positioning cap sealing rim 22 immediately adjacent container periphery 14. This interference fit provides a resealable vent means for the disinfecting apparatus.

In operation, once gas vents to a point outside the container-cap seal (defined by the container periphery/cap sealing rim interface), the gas may escape via a variety of venting means. For example, the gas may escape through a loosely-fitted thread connection between the container-cap threading interface. However, such a venting pathway is not preferred, because the path may be blocked either by the user overtightening the cap onto the container or by foreign material fouling the very thin pathway established between the threads.

A preferred means of venting the gas beyond the container-cap seal is via one or more openings in the cap. The openings are positioned through the cap, at points between the cap sealing rim and the outer periphery of the cap. The openings may have the shape of holes, slits, gratings and the like, or any other shape which does not structurally damage the cap. While the size of the opening may vary substantially, the opening is preferably not large enough to structurally damage the cap, nor small enough to allow minor debris to easily obstruct the opening and inhibit proper venting. Preferably, the cap is provided with at least one substantially circular hole, as shown in FIGS. 1–3, having a diameter of about 0.25 to 3 mm. Hence, cap opening 26 is an integral part of the preferred vent passageway.

The present invention offers substantial advantages over the prior art venting means in the area of manufacturing. In manufacturing the lens disinfecting device of the present invention, only two components must be molded for the venting system, i.e., the cap and the container. A liquid-impermeable seal is established by components on the cap and container, while venting is allowed by deflection of one element on the container. In contrast, many prior art devices require additional components (e.g. posts, filters, or gaskets, which require additional labor and/or equipment to manufacture and/or install.

Thus, one embodiment of the present invention provides an improved method of providing an ophthalmic lens treatment apparatus with a resealable primary venting means to vent excess internal pressure within the apparatus. Generally, the method involves providing a cap with a sealing rim on the side of the cap adapted to mate with said container, in which the cap sealing rim has a predetermined mechanical strength. The method further includes a step of providing a container with a periphery adapted to mate with the cap sealing rim and having a mechanical strength which is less than the cap sealing rim strength. The preferred method of providing reduced strength in the container periphery relative to the cap sealing rim is to provide the container periphery with a reduced thickness relative to the cap sealing rim. In addition, the method involves providing the apparatus with a secondary venting means, capable of allowing gas to vent from a point outside said container-cap seal to a point outside said apparatus. As previously discussed, the preferred secondary vent means includes at least one opening in the cap. One advantage of the aforementioned method is that both the cap (including sealing rim and secondary vent means) and container may be formed by injection molding, without additional assembly or handling.

The present venting system also provides operational advantages based on the simplicity of operation. First, the vent passageway is difficult to obstruct in the present system. Cap opening 26 is sufficiently large not to be easily obstructed, as opposed to prior art filters, posts in bores, and the like. Further, the container-cap seal extends in a circular fashion over a wide circumference which is also difficult to obstruct. Second, the vent passageway of the present invention is formed without the operation of complicated mechanical action. More complex mechanical venting systems may fail for a number of reasons, such as debris blocking movement, corrosion, etc. Thus, the operational simplicity of the present invention offers improvements in consistency and predictability of operation.

The invention has been described in detail, with reference to certain preferred embodiments, in order to enable the reader to practice the invention without undue experimentation. However, a person having ordinary skill in the art will readily recognize that many of the previous components and parameters may be varied or modified to a certain extent without departing from the scope and spirit of the invention. Furthermore, titles, headings, or the like are provided to enhance the reader's comprehension of this document, and should not be read as limiting the scope of the present invention. Accordingly, the intellectual property rights to this invention are defined only by the following claims.

That which is claimed is:

1. An apparatus for treating ophthalmic lenses, comprising:

(a) a container adapted to receive a treating solution, said container having an end including a substantially circular periphery defining an opening which is adapted to receive a lens retaining means;

(b) a cap adapted to be affixed to said container at said open end, in order to provide a substantially liquid-impermeable seal, said cap further including a sealing rim adapted to mate with said container periphery, said cap and said container defining an apparatus for treating ophthlalmic lenses, wherein said container periphery is sufficiently flexible to at least partially deform to allow gas to escape between said container periphery and said cap sealing rim when the gas pressure within said container exceeds a predetermined pressure above atmospheric pressure, said container periphery and said sealing rim thereby forming a primary sealing and venting means, and wherein said apparatus further includes a secondary venting means which allows gas passing from said container through said primary sealing and venting means to pass to the surroundings.

2. An apparatus of claim 1, wherein the external diameter of said cap sealing rim is sufficiently larger than the internal diameter of said container periphery that said container periphery deforms slightly when mated with said cap sealing rim, thereby providing a seal to said container which is substantially impermeable to liquid and gas in the absence of excessive internal pressure.

3. An apparatus of claim 1, wherein said secondary venting means is defined by at least one opening extending through said cap, between said cap sealing rim and the periphery of said cap, and wherein said container periphery is sufficiently flexible to allow gas to escape between said container periphery and said cap sealing rim, and wherein said gas continues through said cap opening, when the gas pressure within said container exceeds a predetermined pressure above atmospheric pressure.

4. An apparatus of claim 1, wherein said cap opening is selected from the group consisting of holes, slits, gratings, and combinations thereof.

5. An apparatus of claim 4, wherein said opening is a substantially circular hole which extends through said cap.

6. An apparatus of claim 5, wherein said hole has a diameter of about 0.25 to 3 mm.

7. An apparatus of claim 1, wherein said container periphery includes external threading and said cap periphery includes internal threading adapted to mate with said threading on said container periphery.

8. An apparatus of claim 7, wherein said mating threading is loosely mated to define said secondary venting means.

9. An apparatus of claim 1, wherein said ophthalmic lens is a contact lens.

10. An apparatus of claim 1, wherein said container periphery has a thickness of 0.3 to 1.5 mm along a cross-section substantially parallel with the plane defined by the container opening.

11. An apparatus of claim 10, wherein said container periphery has a thickness of 0.6 to 0.9 mm along a cross-section substantially parallel with the plane defined by the container opening.

12. An apparatus of claim 1, wherein said container periphery is thinner than the container body, and wherein said container periphery having said reduced thickness extends about 1 to 10 mm from said container opening.

13. An apparatus of claim 1, wherein said container is formed from a polymeric material selected from the group consisting of polypropylene, polyethylene, copolymers and mixtures thereof.

14. An apparatus of claim 1, wherein said cap sealing rim has a thickness 0.75 to 2.5 mm along a cross-section substantially parallel with the plane defined by the end of the cap sealing rim.

15. An apparatus of claim 14, wherein said cap sealing rim has a thickness 1 to 2 mm along a cross-section substantially parallel with the plane defined by the end of the cap sealing rim.

16. An apparatus of claim 1, wherein said cap further includes a lens retaining means affixed thereto in an orientation such that said lens retaining means is positioned within said container when said cap is affixed to said container.

17. An apparatus of claim 16, wherein said apparatus further includes a catalytic component which catalyzes the conversion of a disinfectant into at least one gaseous product, wherein said catalytic component is affixed to said lens retaining means.

18. An apparatus of claim 2, wherein said secondary venting means is defined by at least one opening extending through said cap, between said cap sealing rim and the periphery of said cap, and wherein said container periphery is sufficiently flexible to allow gas to escape between said container periphery and said cap sealing rim, and wherein said gas continues through said cap opening, when the gas pressure within said container exceeds a predetermined pressure above atmospheric pressure;

wherein said container periphery includes external threading and said cap periphery includes internal threading adapted to mate with said threading on said container periphery;

wherein said container body has a thickness greater than said container periphery;

wherein said cap sealing rim has a thickness greater than said container periphery.

19. A method of forming an apparatus for treating ophthalmic lenses, said apparatus including a container and a mating cap, wherein the mating of said container to said cap defines an internal cavity, wherein said mating provides a liquid and gas impermeable seal for said cavity below a first predetermined internal pressure, and wherein said apparatus is capable of providing a resealable vent passageway to allow excessive gas to vent at a second predetermined internal pressure, said method comprising the steps of:

(a) forming a container adapted to receive a disinfecting solution, said container having an end having a substantially circular periphery defining an opening which is adapted to receive a lens retaining means, said container periphery having a thickness which is less than the thickness of the container body; and (b) forming a cap adapted to be affixed to said container at said end having said opening, in order to provide a substantially liquid-impermeable seal, said cap including a sealing rim adapted to mate with said container periphery;

said cap and said container defining an apparatus for treating ophthlalmic lenses, wherein said container periphery is sufficiently flexible to allow gas to escape between said container periphery and said cap sealing rim when the gas pressure within said container exceeds a predetermined pressure above atmospheric pressure, said container periphery and said sealing rim thereby forming a primary sealing and venting means, and wherein said apparatus further includes a secondary venting means which allows gas passing from said container through said primary sealing and venting means to pass to the surroundings.

20. A method of claim 19, wherein said forming steps are injection molding steps.

21. A method of claim 20, wherein said cap has at least one opening extending through said cap, between said cap sealing rim and the periphery of said cap, and wherein said container periphery is sufficiently flexible to allow gas to escape between said container periphery and said cap sealing rim, and wherein said gas continues through said cap opening, when the gas pressure within said container exceeds a predetermined pressure above atmospheric pressure.

22. A method of claim 21, wherein said opening is a substantially circular hole which extends through said cap.

23. A method of claim 22, wherein said hole is formed during said injection molding of said cap.

24. A method of claim 22, wherein said hole is formed by mechanically drilling said hole through said cap subsequent to the injection molding of said cap.

25. A method of providing an ophthalmic lens treatment apparatus with a resealable vent means to vent excess internal pressure within the apparatus, said apparatus including a container having an opening defined by the container periphery at one end and a cap adapted to mate with said container, comprising the steps of:

(a) providing a cap with sealing rim on the side of the cap adapted to mate with a container, said cap sealing sealing rim having a predetermined mechanical strength;

(b) providing said container with a periphery adapted to mate with said cap sealing rim and having a mechanical strength which is less than the cap sealing rim strength; said cap and said container defining an apparatus for treating ophthalmic lenses, wherein the mating of said container periphery to said cap sealing rim provides a primary sealing and venting means for said container, which sealing and venting means is substantially impermeable to gas or liquid in the absence of a condition in which the internal pressure exceeds the external pressure, whereby said seal may be breached by excess internal pressure, thereby allowing gas to pass from said container to a point outside said seal; and (c) providing said apparatus with a secondary vent means, capable of allowing gas to vent from a point outside said container-cap seal to a point outside said apparatus, wherein excess internal pressure causes said container periphery to at least partially deform, thereby allowing gas from within the container to vent through the resealable seal and through said secondary vent means to a point outside said apparatus.

26. A method of claim 25, wherein said cap and said container are formed by injection molding.

* * * * *